United States Patent
Dubey et al.

(10) Patent No.: US 7,713,216 B2
(45) Date of Patent: May 11, 2010

(54) METHOD FOR CERVICAL DILATION AND/OR MEASUREMENT

(75) Inventors: Dharmesh Dubey, Jacksonville, FL (US); Tim Báird, Ponte Vedra Beach, FL (US)

(73) Assignee: Intrapartum, LLC, Jacksonville, FL (US)

(*) Notice: Subject to any disclaimer, the term of this patent is extended or adjusted under 35 U.S.C. 154(b) by 270 days.

(21) Appl. No.: 11/401,623

(22) Filed: Apr. 10, 2006

(65) Prior Publication Data

US 2007/0239197 A1    Oct. 11, 2007

(51) Int. Cl.
*A61B 5/103* (2006.01)
*A61B 5/117* (2006.01)

(52) U.S. Cl. ....................... 600/588; 600/591

(58) Field of Classification Search ............. 600/586, 600/587, 591, 588
See application file for complete search history.

(56) References Cited

U.S. PATENT DOCUMENTS

| | | | |
|---|---|---|---|
| 2,642,672 A | 6/1953 | Lewis et al. | |
| 2,924,220 A | 2/1960 | Von Micsky | |
| 3,273,559 A | 9/1966 | Evans | |
| 3,312,222 A * | 4/1967 | Dwyer | 606/121 |
| 3,606,879 A | 9/1971 | Estes | |
| 3,626,949 A | 12/1971 | Shute | |
| 3,768,459 A | 10/1973 | Cannon et al. | |
| 4,141,345 A | 2/1979 | Allen et al. | |
| 4,207,902 A | 6/1980 | Krementsov | |
| 4,245,656 A | 1/1981 | Farr et al. | |
| 4,362,167 A | 12/1982 | Nicolai et al. | |
| 4,611,603 A | 9/1986 | Kelso et al. | |
| 4,682,609 A | 7/1987 | Parsons | |
| 4,719,925 A | 1/1988 | Parsons | |
| 4,805,628 A | 2/1989 | Fry et al. | |
| 4,986,980 A | 1/1991 | Jacobsen | |
| 5,143,505 A | 9/1992 | Burdea et al. | |
| 5,222,485 A | 6/1993 | Jerath | |
| 5,275,169 A | 1/1994 | Afromowitz et al. | |
| 5,301,680 A | 4/1994 | Rosenberg | |
| 5,354,162 A | 10/1994 | Burdea et al. | |
| 5,373,846 A | 12/1994 | Wilder | |
| 5,373,852 A | 12/1994 | Harrison et al. | |

(Continued)

FOREIGN PATENT DOCUMENTS

DE    4137751 A1    5/1993

(Continued)

*Primary Examiner*—Max Hindenburg
*Assistant Examiner*—H. Q. Nguyen
(74) *Attorney, Agent, or Firm*—Christopher & Weisberg, P.A.

(57) ABSTRACT

The present invention provides a medical device for measuring and/or providing cervical dilation including an elongate body defining a proximal end and a distal end, as well as an expandable element coupled to the distal end of the elongate body. An array of movable elements may be disposed circumferentially about the elongate body, where the array of movable elements is movably coupled to the distal end of the elongate body by a plurality of wires. The medical device may further include a measurement mechanism able to determine a radial spacing of the array of movable elements, as well as a dilation indicator in communication with the measurement mechanism. One or more pressure sensors may be coupled to the array of movable elements, whereby a control element is in communication with the pressure sensors. In addition, an inflation source may be included in fluid communication with the expandable element.

16 Claims, 8 Drawing Sheets

U.S. PATENT DOCUMENTS

| | | | |
|---|---|---|---|
| 5,405,356 A | 4/1995 | Hahn et al. | |
| 5,406,961 A | 4/1995 | Artal | |
| 5,438,996 A | 8/1995 | Kemper et al. | |
| 5,450,857 A | 9/1995 | Garfield et al. | |
| 5,658,295 A | 8/1997 | Krementsov | |
| 5,713,371 A | 2/1998 | Sherman et al. | |
| 5,807,281 A | 9/1998 | Welch | |
| 5,807,376 A | 9/1998 | Viola et al. | |
| 5,829,438 A | 11/1998 | Gibbs et al. | |
| 5,851,188 A | 12/1998 | Bullard et al. | |
| 5,867,831 A | 2/1999 | Husain | |
| 5,876,357 A | 3/1999 | Tomer | |
| 5,924,175 A * | 7/1999 | Lippitt et al. | 24/537 |
| 5,935,061 A | 8/1999 | Acker et al. | |
| 6,039,701 A * | 3/2000 | Sliwa et al. | 600/588 |
| 6,066,104 A | 5/2000 | Dao et al. | |
| 6,110,200 A | 8/2000 | Hinnenkamp | |
| 6,123,923 A | 9/2000 | Unger et al. | |
| 6,200,279 B1 | 3/2001 | Paltieli | |
| 6,231,834 B1 | 5/2001 | Unger et al. | |
| 6,261,247 B1 | 7/2001 | Ishikawa et al. | |
| 6,270,458 B1 | 8/2001 | Barnea | |
| 6,363,271 B1 | 3/2002 | Berry | |
| 6,383,137 B1 | 5/2002 | Berry | |
| 6,419,646 B1 | 7/2002 | Baxter-Jones | |
| 6,423,000 B1 | 7/2002 | Berry | |
| 6,423,016 B1 | 7/2002 | Hamilton et al. | |
| 6,425,899 B1 | 7/2002 | Biehl | |
| 6,450,977 B1 | 9/2002 | Baxter-Jones | |
| 6,451,042 B1 | 9/2002 | Bonutti | |
| 6,524,249 B2 | 2/2003 | Moehring et al. | |
| 6,526,669 B2 | 3/2003 | Nagata | |
| 6,567,990 B1 | 5/2003 | Spitznagle | |
| 6,569,108 B2 | 5/2003 | Sarvazyan et al. | |
| 6,592,315 B2 | 7/2003 | Osborne, Jr. | |
| 6,669,653 B2 | 12/2003 | Paltieli | |
| 6,802,817 B2 | 10/2004 | Baxter-Jones et al. | |
| 6,866,643 B2 | 3/2005 | Kramer | |
| 7,042,438 B2 | 5/2006 | McRae et al. | |
| 7,150,108 B2 | 12/2006 | Babb | |
| 2001/0039388 A1 | 11/2001 | Korotko et al. | |
| 2001/0040550 A1 | 11/2001 | Vance et al. | |
| 2003/0114779 A1 | 6/2003 | Paltieli | |
| 2003/0229267 A1 | 12/2003 | Belson et al. | |
| 2004/0068203 A1 | 4/2004 | Gellman et al. | |
| 2004/0210136 A1 * | 10/2004 | Varghese et al. | 600/443 |
| 2004/0225235 A1 | 11/2004 | Ben-Cnaan et al. | |
| 2004/0236193 A1 | 11/2004 | Sharf | |
| 2005/0027215 A1 | 2/2005 | Baxter-Jones et al. | |
| 2005/0038340 A1 | 2/2005 | Vaezy et al. | |
| 2005/0049509 A1 * | 3/2005 | Mansour et al. | 600/476 |
| 2005/0055043 A1 * | 3/2005 | Foltz et al. | 606/193 |
| 2005/0113852 A1 | 5/2005 | Burbank et al. | |
| 2005/0149114 A1 * | 7/2005 | Cartledge et al. | 606/213 |
| 2006/0064038 A1 | 3/2006 | Omata et al. | |
| 2006/0129070 A1 | 6/2006 | Pearl et al. | |

FOREIGN PATENT DOCUMENTS

| | | |
|---|---|---|
| EP | 0752 233 | 1/1997 |
| GB | 2 137 499 A | 10/1984 |
| GB | 2137499 A | 10/1984 |
| WO | 9742871 A1 | 11/1997 |
| WO | 9809565 A1 | 3/1998 |
| WO | WO 98/09565 A | 3/1998 |
| WO | 2004006767 A2 | 1/2004 |
| WO | WO 2004/006767 A | 1/2004 |
| WO | 2004062526 A2 | 7/2004 |
| WO | WO 2004/062526 A | 7/2004 |
| WO | 2005020814 A1 | 3/2005 |
| WO | WO 2005/020814 A | 3/2005 |
| WO | 2005070061 A2 | 8/2005 |
| WO | WO 2005/084745 A1 | 9/2005 |

* cited by examiner

METHOD FOR CERVICAL DILATION AND/OR MEASUREMENT

CROSS-REFERENCE TO RELATED APPLICATION

This application is related to and claims priority to pending Utility patent application Ser. No. 11/321,061, filed Dec. 29, 2005, entitled CERVIMETER, the entirety of which is incorporated herein by reference.

STATEMENT REGARDING FEDERALLY SPONSORED RESEARCH OR DEVELOPMENT n/a

FIELD OF THE INVENTION

The present invention relates to obstetric devices and more particularly, to a method and apparatus for measuring cervical dilation during pregnancy.

BACKGROUND OF THE INVENTION

During the later stages of pregnancy, the cervix typically undergoes numerous physical changes which provide increased safety and ease with which the fetus can be delivered. Particularly, the cervical canal tissue softens and increases in pliability, and subsequently, the diameter of the cervical canal begins to increase. Eventually, the dilation of the cervix is completed, allowing for the unobstructed passage of the fetus.

During these stages of pregnancy, there are instances when the cervix fails to dilate sufficiently to allow for the safe and unobstructed passage of the fetus. Such conditions may lead to a need for forced or supplemental dilation of the cervix either mechanically or through medication.

Typically, several mechanical and medical options have been available for creating cervical dilation, either to assist in the management of labor in obstetrical patients, or to assist in the management of gynecological patients requiring operative procedures involving the cervix and uterus. Mechanical solutions employed in assisting the dilation of the cervix include the use of laminaria, which is an organic product that expands gradually upon absorption of moisture, catheters having expandable elements disposed on them, and other related apparatuses. Additional devices employed in assisting the dilation of gynecologic patient have primarily included the use of graduated steel dilators. Although these dilators can be effective in creating dilatation of the cervix, such dilators pose the risk of uterine perforation as a potential complication. Furthermore, while these instruments and methods may have been variably effective, some have been associated with increased risk of infection. In addition, due to a relative lack of precise control, these devices and methods may have an increased probability of producing inaccurate, imprecise, and undesired end results.

The administration of medication to increase cervical dilation has included delivery of prostaglandin agents as well as synthetic oxytocin to create cervical "ripening" and dilatation. However, side effects differ and the appropriateness and/or effectiveness of certain medications may vary between patients.

Considering the risk of infection, perforation and probability of inaccurate or undesired end results of cervical dilation with the methods and devices described above, it would be desirable to provide for precise and accurate cervical dilation having a reduced risk of injury and/or infection.

SUMMARY OF THE INVENTION

The present invention advantageously provides a method and system for the accurate and precise measuring of cervical dilation during labor, as well as a method and system for performing cervical dilation. The medical device of the present invention may include an elongate body defining a proximal end and a distal end, with the elongate body further including an inflation lumen. An expandable element may be coupled to the elongate body in fluid communication with the inflation lumen, and an array of movable elements may be circumferentially disposed about the elongate body, with the array of movable elements being movably coupled to the elongate body by a plurality of wires. The medical device may also include a measurement mechanism able to determine a radial spacing of the array of movable elements, where the measurement mechanism can include a tension ring coupled to the plurality of wires. In addition, a dilation indicator can be provided in communication with the measurement mechanism, while at least one pressure sensor may be coupled to at least one of the array of movable elements. Moreover, a distal pressure sensor can be coupled to the distal end of the elongate body, with the medical device also providing a control element in communication with the at least one pressure sensor and the distal pressure sensor. The medical device can also include an inflation source in fluid communication with the expandable element, as well as an exhaust valve in fluid communication with the expandable element. Furthermore, the medical device may include a camera as well as a lighting element coupled to the distal end of the elongate body, thereby providing visual feedback to aid in the positioning of the device.

In an alternative embodiment, the present invention also provides a cervical dilation sensor to aid in the manual, two-finger approach commonly employed. The cervical dilation sensor may include a first rod, a second rod, and a sensor housing. The first and second rods may be rotatably and pivotably coupled to the sensor housing, as to freely move about the housing in at least two planes of motion. The sensor housing may include one or more sensors coupled to the first and second rods as to measure the relative movement of the two rods, while the cervical dilation sensor may also include a control monitor in communication with the one or more sensors in the sensor housing for displaying and monitoring information provided by the sensors.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
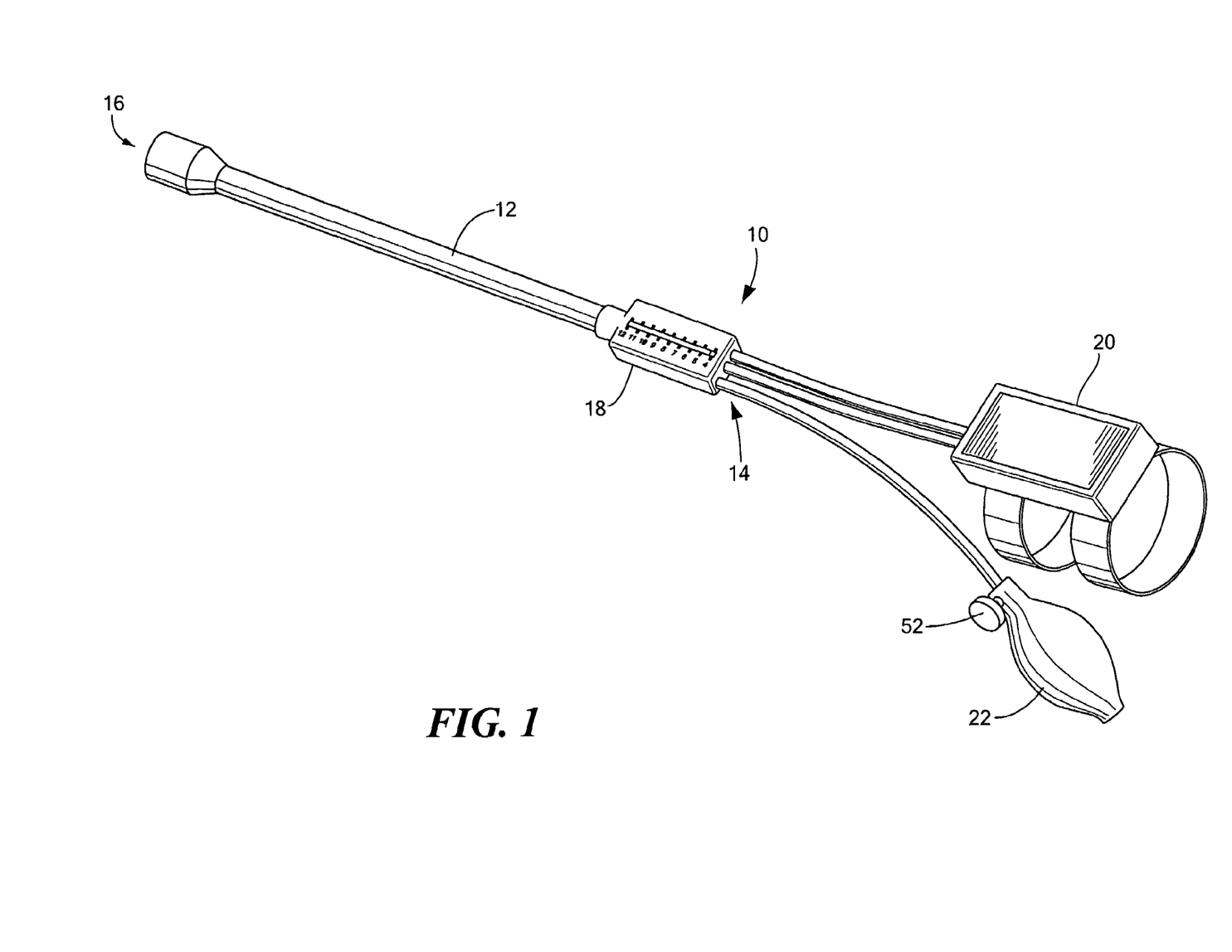
FIG. 1 is an illustration of an embodiment of a medical device in accordance with the present invention.

As shown in FIG. 1, the present invention provides a medical device 10 for measuring and performing cervical dilation. The medical device 10 includes an elongate body 12 defining a proximal end 14 and a distal end 16. The medical device 10 may further include a dilation indicator 18 coupled to the proximal end 14 of the elongate body 12 that is capable of providing a visual indicator of the dilation measurement made by the medical device 10, as well as a control element 20 and an inflation source 22, which will be discussed in more detail below.

Figure 2:
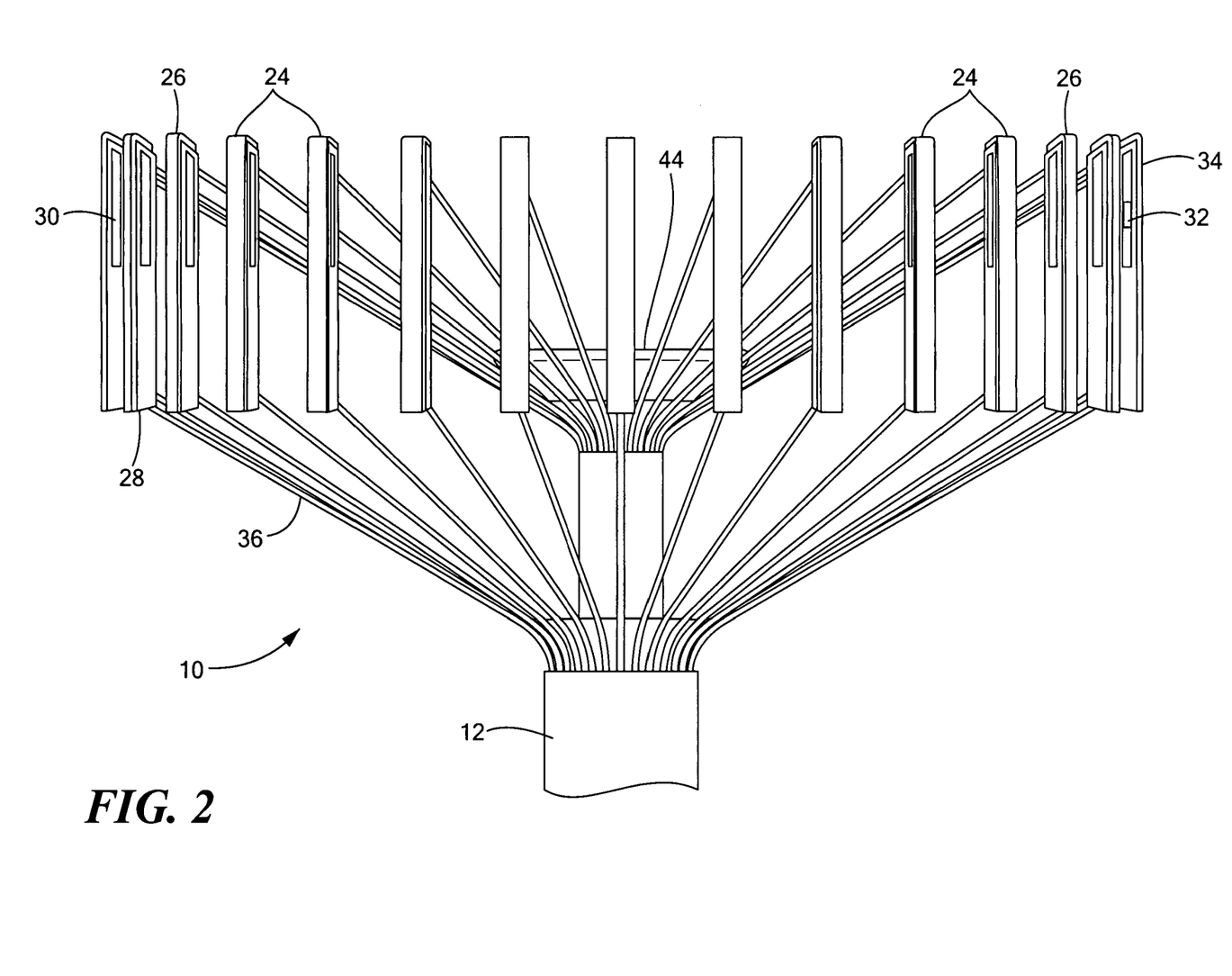
FIG. 2 is a side view of a distal end of the medical device of FIG. 1.

Now referring to FIG. 2, the medical device 10 may further include an array of movable elements 24 disposed circumferentially about an axis of the elongate body 12, where the array of movable elements 24 is located in proximity to the distal end 16 of the elongate body 12. The array of movable elements 24 are movable in a radial direction as to expand and contact with the tissue of the cervix when positioned for measurement of cervical dilation. Moreover, the array of movable elements 24 may be retracted upon completion of the desired measurement to ease the withdrawal of the medical device 10 from the patient. Each movable element may define an upper portion 26 and a lower portion 28. In addition, each movable element may define a channel 30 such that one or more pressure sensors 32 may be mounted or otherwise positionable within the channel 30 of the movable element. Moreover, an outer cushion 34 may be coupled to an outer surface of each movable element, where the outer cushion 34 may be constructed from a gel-like material or other suitable padding. The array of movable elements 24 may further be movably coupled to the elongate body 12 of the medical device 10 by a plurality of wires 36 coupled to the upper and lower portion 28s of the movable elements 24, where the plurality of wires 36 further extend through a length of the elongate body 12.

While the array of movable elements 24 may be extended and retracted by manipulating the plurality of wires 36, an actuating mechanism may be provided to facilitate movement of the array of movable elements 24 from a retracted position to an extended position, and vice versa. The actuating mechanism may include a spring mechanism, a telescoping element, or, alternatively, the medical device 10 may include an expandable element 38, such as a balloon. Now referring to FIG. 3, the medical device 10 of the present invention may further include the expandable element 38 coupled to or otherwise disposed on the elongate body 12 at or near the distal end 16 of the elongate body 12. The expandable element 38 may be configured in a myriad of shapes, including a toroidal configuration in which the expandable element 38 defines a ring-like, "O" shape. Moreover, an inflation lumen 40 can be included in fluid communication with the expandable element 38, where the inflation lumen 40 is disposed within and traverses a substantial length of the elongate body 12.

Figure 3:
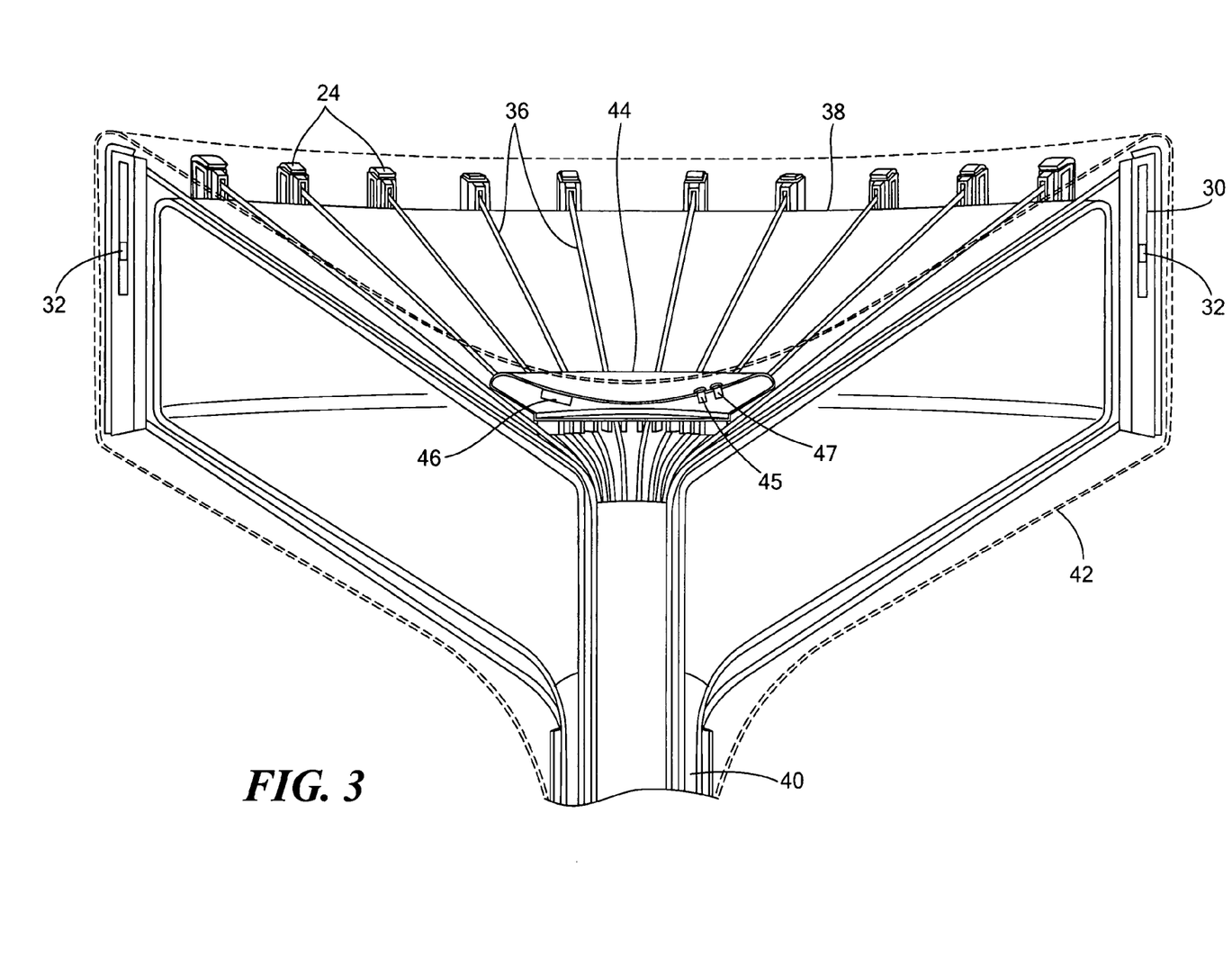
FIG. 3 is a cross-sectional view of a distal end of the medical device of FIG. 1.

The medical device 10 of the present invention may include additional features providing safety, ease of use, and the like. For example, the medical device 10 may include a protective sheath 42 encasing at least a portion of the distal end 16 of the elongate body 12. The sheath 42 may include one or more layers of various materials to provide a water-tight seal around the medical device, as well as adding to patient comfort by having additional padding and/or a lubricious coating to ease positioning of the device. For example, a first layer may completely enclose the medical device to ensure the device is not exposed to external fluids or objects. A second layer may be placed over the first layer as a protective layer which is removable by a physician or operator after each use, thereby providing a sterile layer and the possibility for re-use of the medical device. A third layer may be provided over the second layer and include a lubricious property allowing for smooth insertion, operation, and removal of the device.

Furthermore, a distal pad 44 may be coupled to the elongate body 12 at or near the distal end 16, where the distal pad 44 may be contoured or shaped to conform to the curvature of the head of a baby. In addition, a distal pressure sensor 46 may be coupled to the distal pad 44 to aid in monitoring the positioning of the medical device 10 and for determining contact with the cervix or with the baby. The distal pad 44 and distal pressure sensor 46 may provide feedback to a physician and aid in the axial positioning of the medical device 10 upon insertion into a patient. Furthermore, a camera 45 and a lighting element 47 may also be coupled to the distal portion of the medical device. The camera 45 may be a miniaturized instrument or pin-hole camera as commonly employed in endoscopic surgical procedures, while the lighting element 47 may include a diode, fiber optic, or other illumination mechanism as is known in the art. The camera 45 and lighting element 47 may provide visual feedback to a physician to further aid in maneuvering and positioning the medical device when in use.

Figure 4:
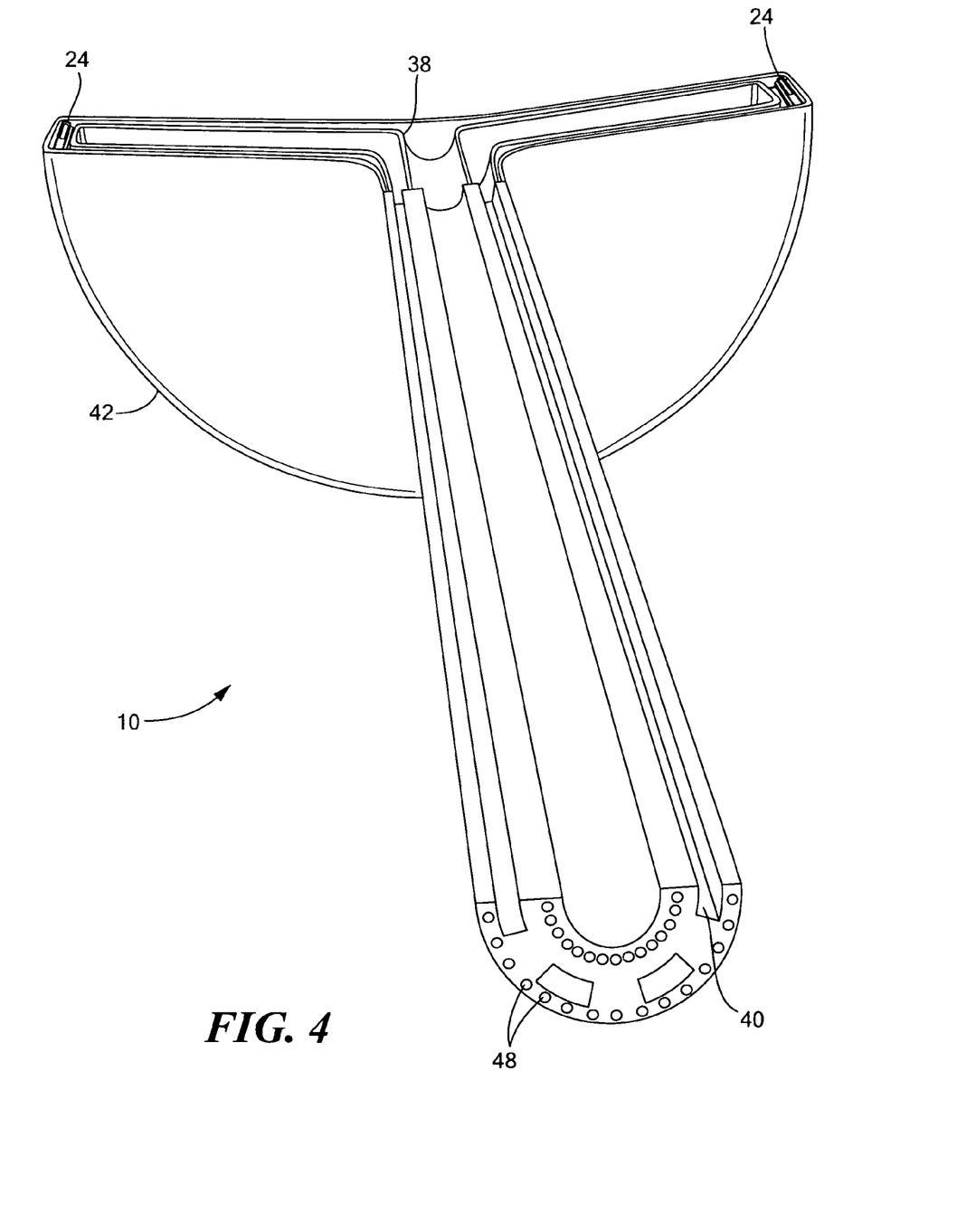
FIG. 4 is an additional cross-sectional view of the medical device of FIG. 1.

As shown in FIG. 4, the elongate body 12 may define a plurality of wire lumens 48 for slideably receiving a portion of each of the plurality of wires 36 coupled to the array of movable elements 24. Each wire of the plurality of wires 36 may be slideably positioned within each of the plurality of wire lumens 48 as to slide freely with little friction, thereby facilitating the movement of the array of movable elements 24 when the medical device 10 is in use. The wires 36 may have sufficient length as to extend through the entire length of the respective wire lumens 48, and may further extend out of the proximal end 14 of the elongate body 12.

Figure 5:
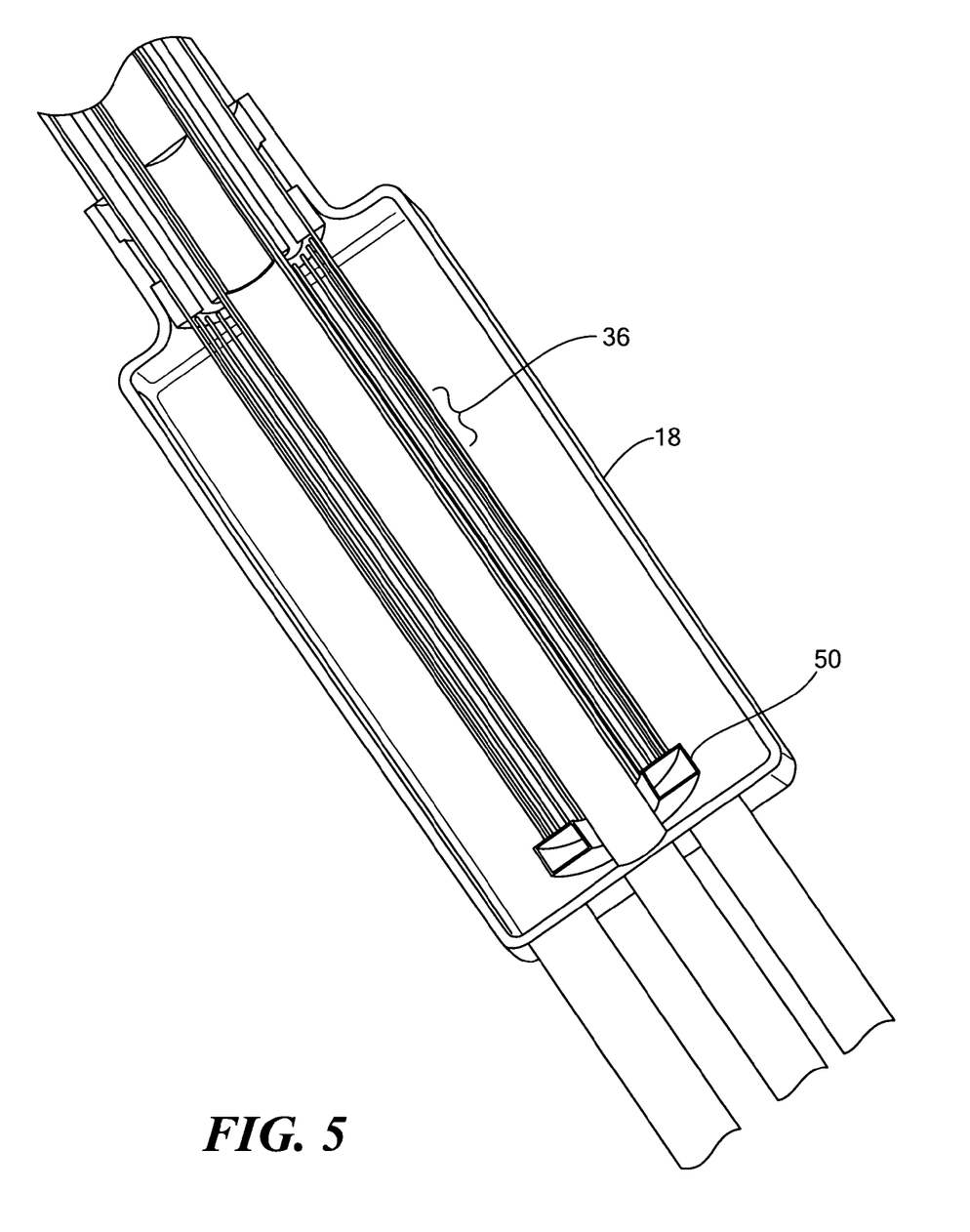
FIG. 5 is a cross-sectional view of an embodiment of a dilation indicator in accordance with the present invention.

The medical device 10 of the present invention may further include a measurement mechanism for monitoring and/or quantifying the movement of the array of movable elements 24 when the medical device 10 is in use. For example, as shown in the FIG. 5 illustration of a cross-section of the dilation indicator 18, the medical device 10 may include a tension ring 50 coupled to the plurality of wires 36 such that the tension ring 50 moves as the wires 36 extend and retract in response to the movement of the array of movable elements 24. The tension ring 50 may further be slideably coupled to the dilation indicator 18, where the dilation indicator 18 conveys a dilation measurement in response to the relative motion of the tension ring 50, the plurality of wires 36, and thus, the array of movable elements 24. The dilation indicator 18 may include predetermined values calculated from the movement of the tension ring 50 as to eliminate the need for a physician to do any calculating to determine the dilation measurement.

Again referring to FIG. 1, in an exemplary system, the proximal end 14 of the medical device 10 of the present invention is coupled to the control element 20 which may be in communication with the numerous sensors provided on the medical device 10, and may also include a visual display to indicate the various operating characteristics and feedback from the device and the included sensors. The control element 20 may include an external console or may further include a wrist-mounted device to ease the overall use of the medical device 10, and may also be in communication with the camera 45 and lighting element 47 coupled to the distal end of the medical device 10. In addition, the inflation source 22 can be provided which may be coupled to the inflation lumen 40 at the proximal end 14 of the elongate body 12, where the inflation source 22 is able to provide a fluid or gas into the inflation lumen 40 for subsequent delivery to the expandable element 38. Examples of suitable inflation source 22s include manual pumps, powered pumps, or the like. Moreover, an exhaust valve 52 may be in fluid communication with both the inflation source 22 as well as the inflation lumen 40 for subsequent control of the release of fluid from the medical device 10.

Figure 6:
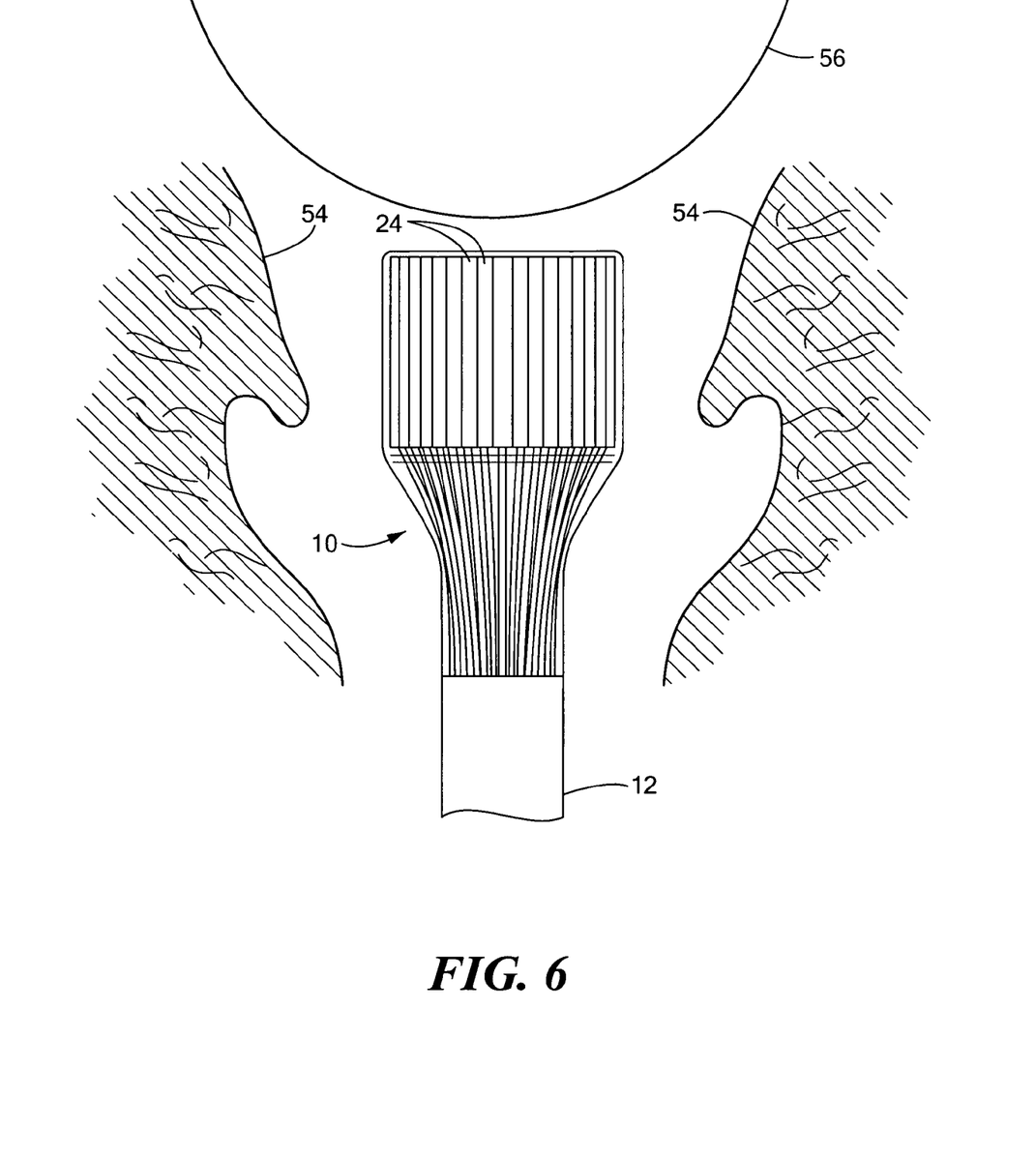
FIG. 6 is an illustration of a distal end of a medical device in a deflated state in accordance with the present invention.
Figure 7:
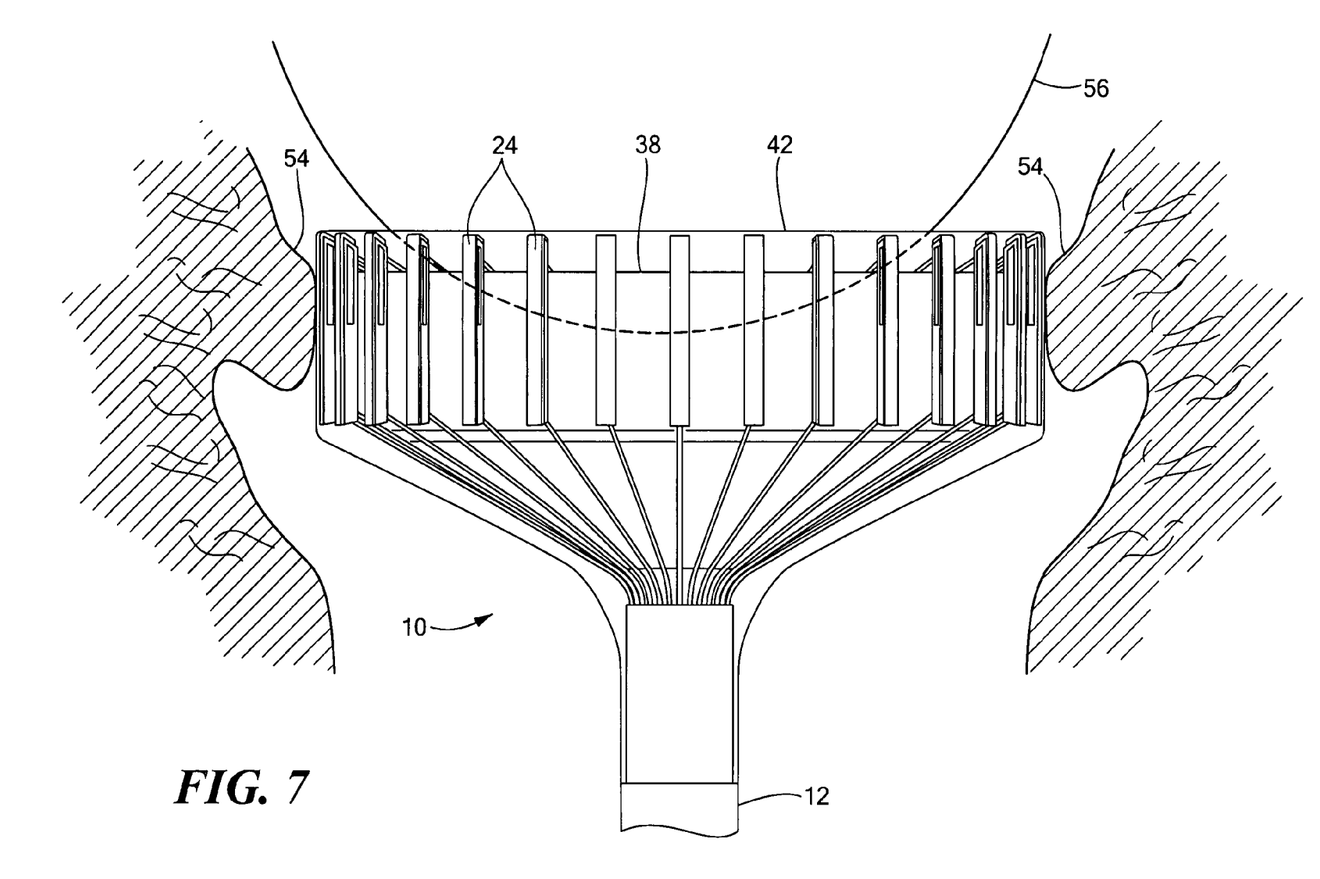
FIG. 7 is an illustration of a distal end of a medical device in an inflated state in accordance with the present invention.
Figure 8:
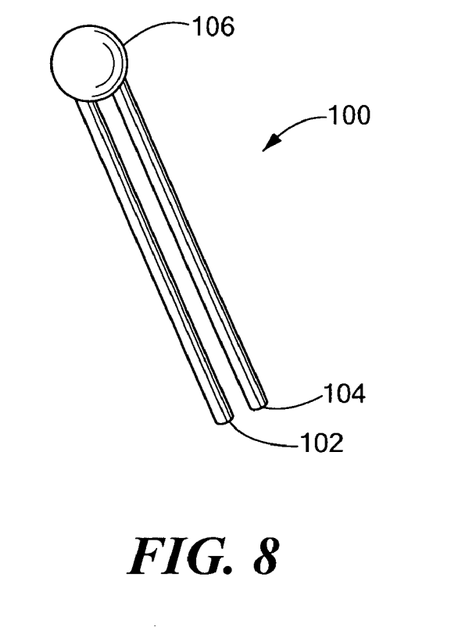
FIG. 8 is a perspective illustration of an embodiment of a cervical dilation sensor in accordance with the present invention.
Figure 9:
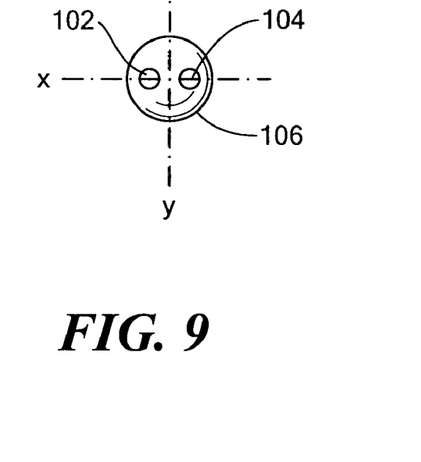
FIG. 9 is a side view of the cervical dilation sensor of FIG. 8.
Figure 10:
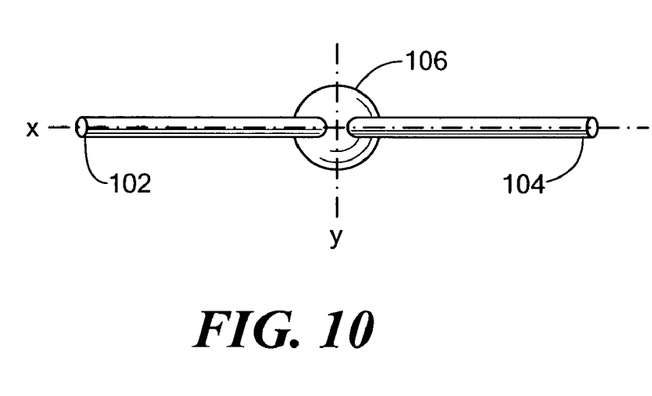
FIG. 10 is an additional illustration of the cervical dilation sensor of FIG. 8.
Figure 11:
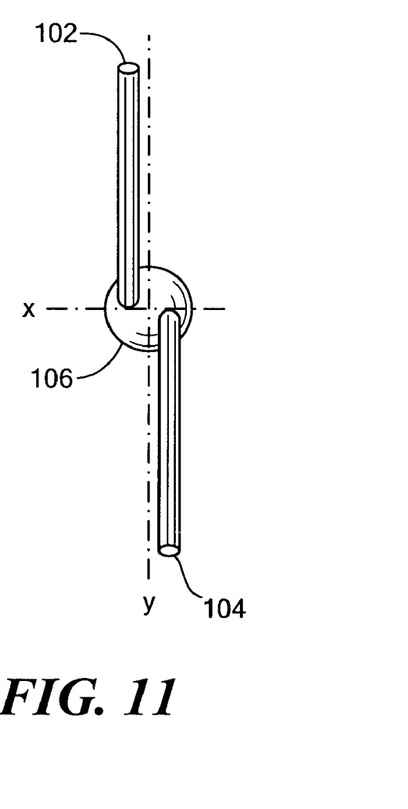
FIG. 11 is yet another depiction of the cervical dilation sensor of FIG. 8.

Referring now to FIGS. 6 and 7, in an exemplary use of the medical device 10 of the present invention, a precise dilation measurement may be performed during the various stages of labor. The medical device 10, in a deflated state, may be positioned such that the distal end 16 of the elongate body 12 is in proximity to the dilated region of the cervix 54. Proper positioning can be aided by feedback provided by the distal pressure sensor 46 when contacting the cervix or the head 56 of the baby, as well as monitoring the visual feedback from the camera 45. Upon proper positioning, the array of movable elements 24 may be extended to contact the tissue of the cervix 54, for example, by actuating the inflation source 22 to inflate the expandable element 38. As the expandable element 38 is inflated and subsequently expands, the array of movable elements 24 located around the periphery of the expandable element 38 will move outward in a radial direction, while lengths of the plurality of wires 36 will be drawn further into the respective plurality of wire lumens 48. As the array of movable elements 24 is coupled to the plurality of wires 36, which are further coupled to the tension ring 50, the expandable element 38 will expand outward uniformly from the elongate body 12.

The inflation source 22 may continue to inflate the expandable element 38 until the movable elements 24 of the medical device 10 come into contact with the dilated or undilated cervix 54. Such contact can be indicated and monitored through information provided by the pressure sensors 32 coupled to the movable elements 24. Furthermore, the control element 20, which is in communication with the sensors, may include an algorithm or computational ability to determine if the pressure sensor feedback indicates a substantially uniform circular state. That is to say, that the pressure measurements from each of the pressure sensors 32 disposed about the movable elements 24 are approximately the same. When the desired inflation level or diameter has been attained as indicated by pressure sensor measurements or from the dilation indicator, the inflation source 22 may be deactivated, or, alternatively, the exhaust valve 52 may be triggered to prevent additional fluid from entering the expandable element 38. Once appropriately inflated, the measuring mechanism and the dilation indicator 18 can provide the dilation measurement as indicated by the distance the plurality of wires 36, and thus the tension ring 50, traveled in reaching the expanded state. As previously stated, the dilation indicator 18 can directly correlate the distance traveled by the wires 36, and thus, the measured expansion of the movable elements 24, to an accurate and precise dilation measurement.

Upon completion of the desired measurement, the movable elements 24 are retracted towards the elongate body 12, i.e., by deflating the expandable element 38 by opening the exhaust valve 52, upon which the movable elements 24 will retract to a closed position for the removal of the medical device 10 from the patient. Both the tension ring 50 and the plurality of wires 36 may be biased towards a closed, retracted position, such that when the expandable element 38 is not under positive inflation pressure, the medical device 10 retains a closed, retracted state. Furthermore, as described above, the medical device 10 may include an outer sheath 42 which, if used, may be removed and replaced for subsequent uses of the medical device 10, thereby providing a re-usable device while maintaining the sterility of the medical environment.

Referring to FIG. 7, in an alternative use of the medical device 10 of the present invention, the distal portion of the medical device 10 may be employed to produce a safe and uniform cervical dilation where a desired dilated condition has not yet occurred or otherwise been achieved. The medical device 10 may be positioned proximate to a region of an undilated cervix and the array of movable elements 24 of the medical device 10 may be expanded to contact the cervical tissue 54. Similar to obtaining a dilation measurement as described above, the distal pad, pressure sensors or camera may provide feedback to a physician or operator to aid in the axial positioning of the device. Through monitoring information from any of the aforementioned components, the medical device may traverse the length of the cervix while reducing the likelihood of accidentally perforating the uterus, which may occur with the use of conventional devices.

Upon initiating the desired contact, the array of movable elements 24 may then be extended further, for example, through a controlled inflation of the expandable element 38, in order to provide a desired rate of expansion, and thus, dilation. Alternatively, the array of movable elements may be actuated to extend outward through pressure or force applied through the plurality of wires 36, or by other actuating mechanisms as known in the art. At any point during the dilation procedure, information may be provided regarding the amount of force being applied to the cervical tissue via the one or more pressure sensors 32 coupled to the array of movable elements 24, as well as the radial spacing of the array of movable elements. As such, through the monitoring of sensor feedback information, the dilating force applied to the array of movable elements either through the plurality of wires 36 or by the expandable element 38 may be appropriately adjusted in order to achieve the desired dilation without unnecessarily damaging the cervical tissue. Additionally, the spacing of the array may be monitored to achieve a desired dilated state. Through the monitoring and manipulation of the operating characteristics of the medical device, including the rate of extension of the array, the pressure between the medical device and the tissue, and/or the distance traveled and thus the radial spacing of the array, a precise and accurate dilation may be induced.

The above-described dilation may be performed for obstetrical uses, for example, in cervical "ripening" to assist in the induction of labor in cases of poorly dilated or effaced cervices. In addition, pre-operative dilation may be performed using the medical device of the present invention in cases of uterine curettage for failed pregnancy, miscarriage, or retained products of conception. Moreover, the medical device may be used for gynecological purposes of cervical dilation in cases of curettage of the endocervix or endometrium, elective termination of pregnancy, diagnostic and operative hysteroscopy, thermal endometrial ablation techniques, as well as treatment of cervical stenosis.

Now referring to FIGS. 8-11, in an alternative embodiment of the present invention, a cervical dilation censor 100 is provided to aid in the manual, two-finger approach of measuring cervical dilation. The cervical dilation sensor 100 may include a first rod 102, a second rod 104, and a sensor housing 106. The first and second rods 102,104 may be rotatably and pivotably coupled to the sensor housing 106, as to freely move about the housing in at least two planes of motion. The sensor housing 106 may include one or more sensors coupled to the first and second rods 102,104 as to measure the movement of the two rods. The cervical dilation sensor 100 may also include a control monitor (not shown) in communication with the one or more sensors in the sensor housing 106 for displaying and monitoring information provided by the sensors.

In an exemplary use, the cervical dilation sensor 100 is coupled to the hand of a physician, with the first rod 102 being paired to the index finger, the second rod 104 being paired to the middle finger, and the sensor housing 106 being positioned in between the two fingers. Subsequently, the physician may position the two fingers and the cervical dilation sensor 100 in proximity to the cervix. Upon reaching the desired location, the two fingers can be spread either into a "V" shape or an "L" shape, and the relative movement of the first and second rods 102,104 will be measured by the one or more sensors in the sensor housing 106. As a result, the physician will not be required to make a subjective observation as to the actual cervical dilation, as the actual width between the spread fingers can be accurately assessed by the cervical dilation sensor 100 and provided to the physician through the control monitor.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method for performing cervical dilation, comprising the steps of:
   providing a medical device having an array of movable elements disposed circumferentially about an axis and a plurality of wires coupled to the array of movable elements;
   positioning the medical device proximate a region of cervical tissue to be dilated; and
   applying a force to the plurality of wires thereby extending the array of movable elements, such that the entirety of each movable element radially extends from the axis to cause dilation of the cervical tissue,
   wherein each movable element is spaced a distance outwardly from the axis, is disposed a distance from an adjacent movable element, and is positioned such that the entirety of each movable element is substantially parallel to the axis about which the array of movable elements is disposed.

2. The method according to claim 1, further comprising the step of measuring a radial spacing of the array of movable elements.

3. The method according to claim 2, wherein the array of movable elements is extended to achieve a radial spacing of a predetermined value.

4. The method according to claim 1, wherein the medical device further includes an expandable element coupled to the away of movable elements, and wherein the step of extending the array of movable elements includes inflating the expandable element.

5. The method according to claim 4, wherein the expandable element has an internal pressure, and wherein the step of extending the away of movable elements includes inflating the expandable element to an internal pressure of a predetermined value.

6. The method according to claim 1, further comprising the step of measuring a pressure level between at least a portion of the medical device and a portion of the cervical tissue.

7. The method according to claim 6, wherein the step of extending the array of movable elements includes extending the array of movable elements until the pressure level reaches a predetermined value.

8. The method according to claim 1, wherein the medical device further includes a distal end, further comprising the step of measuring a pressure level between the distal end and a tissue portion.

9. The method according to claim 8, wherein the step of positioning the medical device proximate a region of cervical tissue to be dilated includes axially positioning the medical device until the pressure level reaches a predetermined value.

10. The method according to claim 1, wherein the medical device further includes a camera, further comprising the step of monitoring the positioning of the medical device with the camera.

11. A method for performing cervical dilation, comprising the steps of:
   providing a medical device having an array of movable elements disposed circumferentially about an axis, a plurality of wires coupled to the array of movable elements, an expandable element coupled to the array of movable elements, and a pressure sensor coupled to the array of movable elements;
   positioning the medical device proximate a region of cervical tissue to be dilated; and
   inflating the expandable element, thereby applying a force to the plurality of wires and extending the array of movable elements, such that the entirety of each movable element radially extends from the axis to cause dilation of the cervical tissue,
   wherein each movable element is spaced a distance outwardly from the axis, is disposed a distance from an adjacent movable element, and is positioned such that the entirety of each movable element is substantially parallel to the axis about which the array of movable elements is disposed.

12. The method according to claim 11, further comprising the step of measuring a pressure level between at least a portion of the medical device and a portion of the cervical tissue.

13. The method according to claim 12, wherein the expandable element is inflated until the pressure level reaches a predetermined value.

14. The method according to claim 11, further comprising the step of measuring a radial spacing of the array of movable elements.

15. The method according to claim 14, wherein the array of movable elements is extended to achieve a radial spacing of a predetermined value.

16. A method for performing cervical dilation, comprising the steps of:
   providing a medical device having an array of movable elements disposed circumferentially about an axis, a plurality of wires coupled to the array of movable elements, an expandable element coupled to the array of movable elements, and a pressure sensor coupled to the array of movable elements;

positioning the medical device proximate a region of cervical tissue to be dilated;

inflating the expandable element, thereby applying a force to the plurality of wires and extending the array of movable elements, such that the entirety of each movable element radially extends from the axis to cause dilation of the cervical tissue, wherein each movable element is spaced a distance outwardly from the axis, is disposed a distance from an adjacent movable element, and is positioned such that the entirety of each movable element is substantially parallel to the axis about which the array of movable elements is disposed;

measuring a pressure level between at least a portion of the medical device and a portion of the cervical tissue; and measuring a radial spacing of the array of movable elements.

* * * * *